(12) United States Patent
Taylor et al.

(10) Patent No.: US 7,794,644 B2
(45) Date of Patent: Sep. 14, 2010

(54) THIN-WALLED OPTICAL OBTURATOR

(75) Inventors: Scott V. Taylor, Mission Viejo, CA (US); John Stout, Irvine, CA (US); Henry Kahle, Trabuco Canyon, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 707 days.

(21) Appl. No.: 11/536,476

(22) Filed: Sep. 28, 2006

(65) Prior Publication Data
US 2007/0075465 A1  Apr. 5, 2007

Related U.S. Application Data

(60) Provisional application No. 60/724,261, filed on Oct. 5, 2005.

(51) Int. Cl.
*B29C 45/36* (2006.01)
(52) U.S. Cl. .................. 264/328.12; 264/328.1
(58) Field of Classification Search ............ None
See application file for complete search history.

(56) References Cited

U.S. PATENT DOCUMENTS

| | | | |
|---|---|---|---|
| 2,301,338 | A | 11/1942 | Smith |
| 2,434,594 | A | 1/1948 | Schultz |
| 3,385,553 | A | 5/1968 | Braun |
| 3,613,684 | A | 10/1971 | Sheridan |
| 4,126,291 | A | 11/1978 | Gilbert et al. |
| 4,150,929 | A | 4/1979 | Brandt |
| 4,750,877 | A | 6/1988 | McFarlane |
| 4,956,143 | A | 9/1990 | McFarlane |
| 5,116,547 | A | 5/1992 | Tsukahara et al. |
| 5,240,397 | A | 8/1993 | Fay et al. |
| 5,391,248 | A | 2/1995 | Brain |
| 5,405,328 | A | 4/1995 | Vidal et al. |
| 5,510,065 | A * | 4/1996 | McFarlane ............ 264/40.5 |

(Continued)

FOREIGN PATENT DOCUMENTS

EP  548612 A1  6/1993

(Continued)

OTHER PUBLICATIONS

PCT/US02/06759 (Pingleton et al.) Published Apr. 3, 2003.*

*Primary Examiner*—Monica A Huson
(74) *Attorney, Agent, or Firm*—Pui Tong Ho; David G. Majdali

(57) ABSTRACT

The invention is directed to a method for manufacturing a thin-wall, single-piece optical obturator having an integral tip and shaft. The invention includes providing an injection mold defining a mold cavity having a core pin positioned within the mold cavity. The mold includes at least one gate and multiple core support pins between the core pin and the mold cavity walls, with at least one primary core support pin positioned on a side opposite the at least one gate. The method also includes injecting a transparent molten polymeric material having high flow properties into the injection mold such that the polymeric material flows between the surface of the mold cavity and the core pin. The core support pins substantially prevent the core pin from shifting while the polymeric material is injected into the mold. The high-flow nature of the polymeric material allows for complete filling of the mold cavity.

55 Claims, 7 Drawing Sheets

U.S. PATENT DOCUMENTS

| | | |
|---|---|---|
| 5,746,734 A | 5/1998 | Dormandy, Jr. et al. |
| 5,980,809 A | 11/1999 | Crain et al. |
| 6,024,551 A | 2/2000 | Yamaguchi |
| 6,043,310 A | 3/2000 | Liu et al. |
| 6,203,745 B1 | 3/2001 | Wachsmann et al. |
| 6,462,111 B1 | 10/2002 | Singh et al. |
| 6,656,198 B2 | 12/2003 | Tsonton et al. |
| 6,770,731 B2 | 8/2004 | Mason et al. |
| 2003/0032755 A1 | 2/2003 | Gorney et al. |
| 2004/0108623 A1 | 6/2004 | Deeter et al. |
| 2004/0199127 A1 | 10/2004 | Jensen et al. |
| 2004/0230217 A1 | 11/2004 | O'Heeron |
| 2005/0033237 A1 | 2/2005 | Fentress et al. |
| 2005/0038466 A1 | 2/2005 | O'Heeron et al. |
| 2005/0065543 A1 | 3/2005 | Kahle et al. |
| 2005/0113533 A1 | 5/2005 | Shaikh et al. |
| 2005/0216028 A1 | 9/2005 | Hart et al. |
| 2005/0288622 A1 | 12/2005 | Albrecht et al. |
| 2006/0041270 A1 | 2/2006 | Lenker et al. |
| 2006/0058570 A1 | 3/2006 | Rapach et al. |

FOREIGN PATENT DOCUMENTS

| | | |
|---|---|---|
| GB | 2124970 A | 2/1984 |
| JP | 08127661 A | 5/1996 |

\* cited by examiner

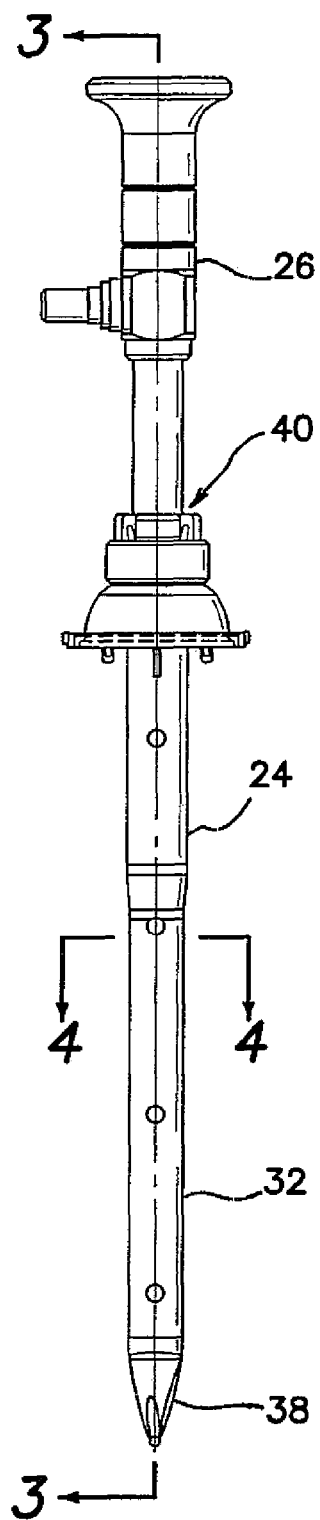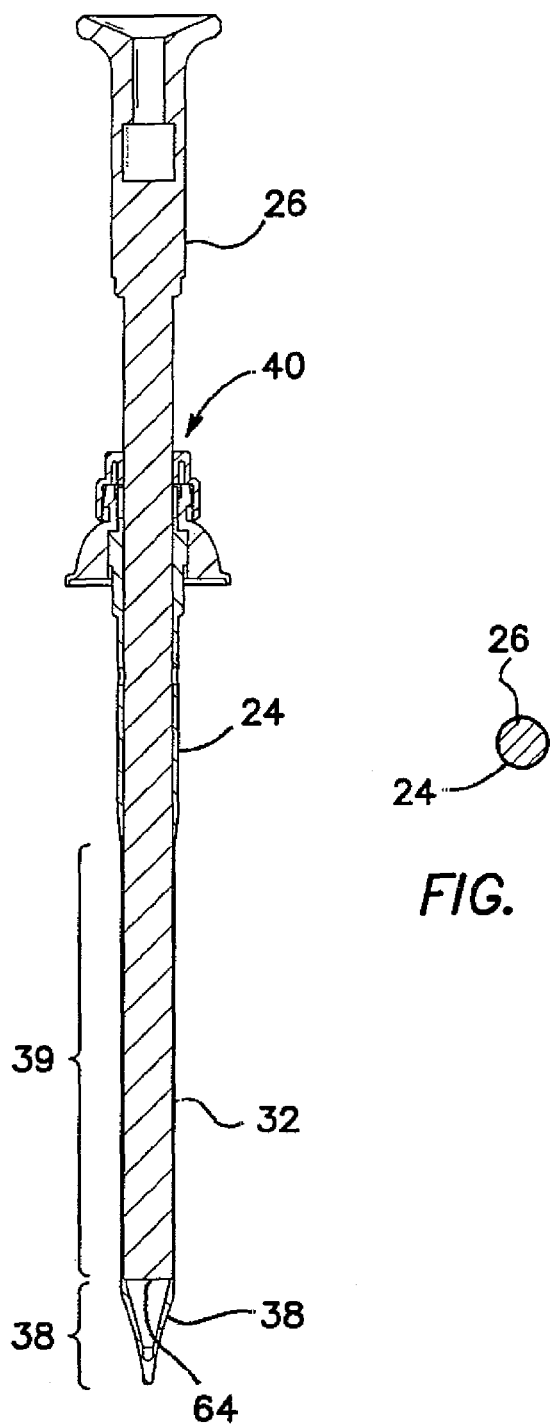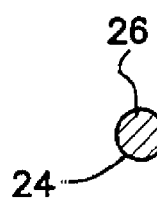
FIG. 2
FIG. 3
FIG. 4

THIN-WALLED OPTICAL OBTURATOR

BACKGROUND

This invention relates generally to trocar systems including obturators and, more specifically, to optical obturators including an integral tip and shaft.

Trocar systems have been of particular advantage in facilitating less invasive surgery across a body wall and within a body cavity. This is particularly true in abdominal surgery where trocars have provided a working channel across the abdominal wall to facilitate the use of instruments within the abdominal cavity.

The trocar systems of the past typically included a cannula, which provides the working channel, and an obturator that is used to place the cannula across the abdominal wall. The obturator is inserted into the working channel of the cannula and pushed through the abdominal wall with a penetration force of sufficient magnitude to result in the penetration of the abdominal wall. Once the cannula is in place, the obturator can be removed.

Some prior art obturators have included a transparent plastic tip that is bonded onto the end of a shaft that is typically metallic, such as a stainless steel shaft. The cost of producing a stainless steel shaft is typically very high due to the cost of fabrication and the raw material cost. Additional cost is incurred to produce the plastic tip and to attach the plastic tip to the shaft. The plastic tips are usually produced through an injection molding process and the tips are typically bonded to the shaft. Other prior art obturators include the metallic shaft with the transparent plastic tip overmolded onto the shaft.

The transparent plastic tip provides the obturator with visualization properties. The optical obturators are configured to enable the insertion of an optical instrument that facilitates visualization of tissue during the insertion of the obturator through a body wall. During use, the optical obturator is typically inserted into a trocar seal and cannula. A conventional laparoscope is then inserted into the proximal end of the optical obturator and advanced to the distal tip of the obturator. An endoscopic video camera may be attached to the proximal end of the laparoscope and the surgeon may axially advance the trocar system through the body wall. As the surgeon advances the trocar through the body wall, the surgeon can visually observe the tissue as it is being traversed via a video monitor that is connected to the endoscopic video camera. The laparoscope facilitates the determination of when the body wall has been completely traversed by the trocar. Once the trocar has traversed the body wall, the obturator and laparoscope may be removed, leaving the trocar seal and cannula disposed across the body wall to provide an access channel into the body cavity for the insertion of laparoscopic instruments.

Other prior art optical obturators are fabricated as a single-piece, including a shaft and an integral tip, and are molded from a transparent material, such as a polymeric material. For instance, some prior art single-piece optical obturators are injection molded. The transparent material of which the optical obturator is formed facilitates visualization of tissue during the insertion of the obturator through a body wall. The shaft portion of the optical obturator extends along an axis between a proximal end and a distal end with a lumen therebetween. The lumen of the shaft is sized and configured to receive a conventional optical instrument, such as a laparoscope For practicality purposes, the outer surface of an optical obturator must be designed to fit within a standard, conventional cannula. The wall thickness of the optical obturator is, therefore, typically determined by the standard sizes of the trocar cannulas and the laparoscopes that have gained acceptance in the surgical environment. For example, one standard size trocar cannula has an inside diameter of 11.5 mm and the optical obturator must be designed to fit within this standard cannula. By way of example, the optical obturator must also be designed to accommodate the insertion of a standard laparoscope, such as a 10 mm laparoscope, into the shaft of the optical obturator to enable the visualization of tissue fibers through the tip of the obturator. Continuing with the example, the outside diameter of the optical obturator may be about 11.4 mm while the inside diameter of the optical obturator may be about 10.1 mm. The diameters in this example result in a very thin wall thickness of about 0.65 mm, and the length of the optical obturator typically ranges from about 205 mm to about 255 mm. Other, smaller, optical obturators may include a length ranging from about 120 mm to about 205 mm and have an outside diameter of about 6.9 mm and an inside diameter of about 5.6 mm, again resulting in a wall thickness of about 0.65 mm. These smaller obturators accommodate 5.5 mm laparoscopes, a common size, and fit into cannulas having an inner diameter of about 7.0 mm. The properties of the materials of which the prior art single-piece optical obturators are fabricated make it difficult to mold a complete part with a thin wall over such a long length; so the shaft portion of the prior art single-piece optical obturators include a relatively thick wall of about 1.18 mm or larger.

Having a thicker wall throughout the length of the shaft increases the overall outside diameter of the trocar assembly. The use of a trocar assembly having a larger overall outside diameter along its length may lead to increased trauma to a patient during use Accordingly, there is a need in the art for a process of fabricating a single-piece optical obturator having a thinner wall than prior art single-piece optical obturators and that can be manufactured at a lower cost in comparison to the prior art multiple-piece optical obturators.

SUMMARY OF THE INVENTION

The invention is directed to a thin-walled, single-piece optical obturator that creates an access channel through a body wall and into a body organ or cavity. The optical obturator is molded from a transparent material that has high-flow properties. The use of the high-flow material enables the injection molding of a single-piece, thin-walled optical obturator including an integral tip and shaft. The optical obturator is configured to enable the insertion of a laparoscope. The laparoscope may include an imaging element and fiber optic light fibers. During use, the optical obturator is inserted into a trocar seal and cannula. A conventional laparoscope may then be inserted into the proximal end of the optical obturator and advanced to the distal tip of the obturator. An endoscopic video camera may be attached to the proximal end of the laparoscope and a surgeon may axially advance the trocar system through the body wall. As the surgeon advances the trocar through the body wall, the surgeon can visually observe the tissue as it is being traversed via a video monitor that is connected to the endoscopic video camera. The surgeon can also readily determine when the body wall has been completely traversed by the trocar. Once the trocar has traversed the body wall, the obturator and laparoscope are removed, leaving the trocar seal and cannula disposed across the body wall to provide an access channel into the body cavity for the insertion of laparoscopic instruments.

In one aspect, the invention includes a method for manufacturing a thin-wall, single-piece optical obturator that has a wall thickness that is less than 1.11 mm. The obturator includes an integral tip and shaft. The shaft extends along an axis between a proximal end and a distal end with a lumen therebetween. The lumen is sized and configured to receive an optical instrument that has a distal end for receiving an image of body tissue. The method includes providing an injection mold. The injection mold includes a mold cavity that defines an outside surface of the single-piece optical obturator. The mold also includes a core pin that is positioned within the mold cavity. The core pin defines an inside surface of the single-piece optical obturator. The distance between an outer surface of the core pin and the surface of the mold cavity is 1.11 mm or less. The mold includes at least one gate that extends into the mold cavity. The mold also includes at least one core support pin that supports the core pin within the mold cavity. The at least one core support pin is positioned between a surface of the mold cavity and a surface of the core pin and on the side substantially opposite the at least one gate. The method further includes injecting a transparent, molten polymeric material that has high flow properties into the injection mold in such manner that the polymeric material flows between the surface of the mold cavity and the core pin.

In one aspect, the method also includes sterilizing the optical obturator with one of gamma radiation, electron beam sterilization and ethylene oxide sterilization. In another aspect, the injecting step includes injecting a high-flow polycarbonate material. In another aspect, the high-flow polycarbonate material is capable of being sterilized by one of gamma radiation, electron beam sterilization and ethylene oxide sterilization. In another aspect, the high-flow polycarbonate material has a compensating colorant. In another aspect, the high-flow polycarbonate material has a melt flow rate of about 20 grams/10 minutes or greater. In another aspect, the high-flow polycarbonate material has a melt flow rate between about 20 grams/10 minutes and about 60 grams/10 minutes. In another aspect, the high-flow polycarbonate material has a weight average molecular weight of about 24000 atomic mass units or lower. In another aspect, the high-flow polycarbonate material has a MOLDFLOW viscosity index of about 196 Pascal-seconds or less at a temperature of about 300° C. In another aspect, the high-flow polycarbonate material has a MOLDFLOW viscosity index of about 196 Pascal-seconds or less at a temperature between about 282° C. and about 316° C. In another aspect, the providing step includes providing an injection mold that has at least two mold sections that define the mold cavity and the core pin is positioned substantially in the center of the mold cavity. In another aspect, the providing step includes providing an injection mold that has two mold halves. In another aspect, the two mold halves define the mold cavity and the core pin is positioned in the mold cavity such that an axis of the core pin is positioned substantially coaxially with an axis of the mold cavity. In another aspect, the plurality of secondary core support pins are included on each half of the mold cavity and distributed along the length of the mold cavity. In another aspect, the secondary core support pins interlock with the core pin. In another aspect, the secondary core support pins are adapted to pilot into the core pin. In another aspect, the secondary core support pins are adapted to pilot into the core pin to a depth of about 0.9 mm. In another aspect, the secondary core support pins are longitudinal and have a substantially circular cross-section along their lengths. In another aspect, the injection mold has four secondary core support pins on each mold half with the secondary core support pins being positioned substantially perpendicular to the core pin and substantially perpendicular to the at least one gate. In another aspect, the injection mold has five secondary core support pins on each mold half with the secondary core support pins being positioned substantially perpendicular to the core pin and substantially perpendicular to the at least one gate. In another aspect, the secondary core support pins are in the form of screws. In another aspect, the ends of the screws that are opposite the heads of the screws are configured for piloting into the core pin. In another aspect, the secondary core support pins are fixedly coupled to the mold halves. In another aspect, the secondary core support pins are adjustably coupled to the mold halves. In another aspect, the providing step includes providing an injection mold that has secondary core support pins positioned substantially perpendicular to the core pin and substantially parallel to the at least one gate on the same side of the mold as the at least one gate. In another aspect, the providing step includes providing an injection mold with the at least one core support pin including at least one primary core support pin that is positioned substantially perpendicular to the core pin and substantially parallel to the at least one gate on the side of the mold opposite the at least one gate. In another aspect, the at least one primary core support pin includes two primary core support pins that are distributed along the length of the mold cavity and positioned substantially perpendicular to the core pin and substantially parallel to the at least one gate on the side of the mold opposite the at least one gate. In another aspect, the at least one primary core support pin includes three primary core support pins that are distributed along the length of the mold cavity and positioned substantially perpendicular to the core pin and substantially parallel to the at least one gate on the side of the mold opposite the at least one gate. In another aspect, the providing step includes providing an injection mold having a plurality of gates distributed along the length of the mold cavity. In another aspect, the injection mold has a series of about three gates. In another aspect, the injection mold has a series of about four gates.

These and other features of the invention will become more apparent with a discussion of the various embodiments in reference to the associated drawings.

DESCRIPTION OF THE DRAWINGS

FIG. 2 illustrates a side view of an optical obturator assembly with a laparoscope inserted into the optical obturator;

FIG. 3 is a longitudinal cross-section view taken along line 3-3 of FIG. 2;

FIG. 4 is a radial cross-section view taken along line 4-4 of FIG. 2;

DESCRIPTION

Figure 1:
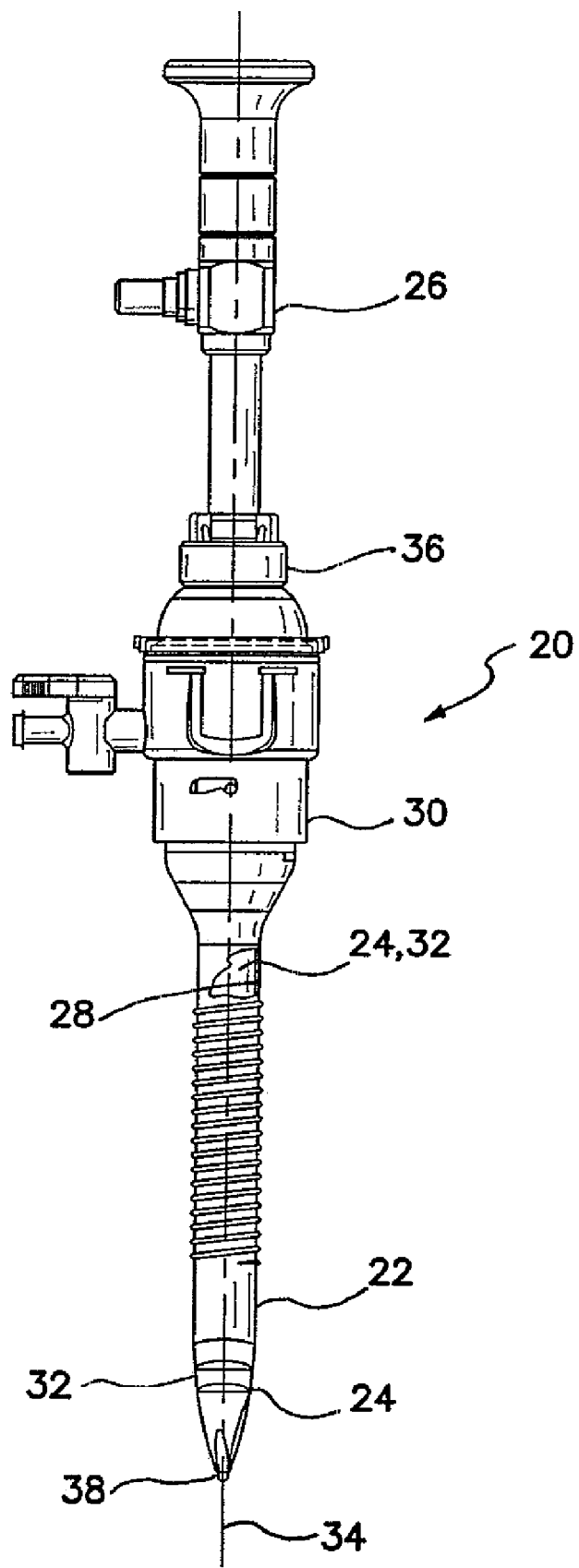
FIG. 1 illustrates a side view of an optical trocar system including an optical obturator inserted into a cannula and a laparoscope inserted into the optical obturator.

An optical trocar system 20 is illustrated in FIG. 1. The optical trocar system includes a cannula 22, an optical obturator 24, and a laparoscope 26. The cannula defines a working channel 28 and a valve housing 30. The optical obturator includes a shaft 32 extending along an axis 34. A handle 36 is disposed at a proximal end of the shaft while a blunt distal tip 38 is disposed at a distal end of the shaft. Those skilled in the art will appreciate that other obturator tip configurations may be used and are contemplated within the scope of the present invention. Such other tip configurations include full radius, conical, pyramidal, and generally tapered. Also, the tip may include sharp edges or molded blades. The shaft of the optical obturator is sized and configured for disposition within the working channel of the cannula. With this disposition, the optical obturator can be placed across a body wall, such as the abdominal wall, to provide the cannula with access across the wall and into a body cavity, such as the peritoneal or abdominal cavity. The tip of the optical obturator serves to direct the optical obturator through the abdominal wall and the peritoneum and the optical obturator may be removed once the cannula is operatively disposed with the working channel extending into the abdominal cavity. The diameter of the shaft can range from about 3 mm to about 20 mm and is designed to fit within a trocar seal and the cannula.

Referring to FIGS. 2 through 4, the optical obturator 24 of the invention is designed to accommodate the insertion of a conventional laparoscope 26. In particular, the shaft 32 of the optical obturator is hollow to allow for the insertion of the laparoscope at an opening 40. The shaft is sized and configured to allow the laparoscope to slide within proximity of the distal tip 38, thus providing a viewing area through the tip. An endoscopic video camera (not shown) is typically connected to the laparoscope and this combination is connected to a video monitor. By enabling the positioning of the conventional laparoscope within the distal tip of the optical obturator, it is possible to visually observe body tissue as it is being separated by the trocar system 20 (FIG. 1). Visualization of body tissue as it is being separated by the trocar system allows a surgeon to monitor the advancement of the trocar system and to avoid traumatizing vessels or organs. For example, during a laparoscopic cholecystectomy, a trocar is usually placed through the umbilicus of the patient. The placement of this trocar is typically performed in a blind fashion in that the surgeon cannot see where the tip of the trocar is as it is advanced through the abdominal wall and into the abdominal cavity of the patient. This results in a high degree of risk that the trocar may be inadvertently advanced too far into the abdomen of the patient, resulting in trauma to vital organs and/or vessels. By providing a trocar system with visualization properties, this risk is diminished as the surgeon is better able to determine when the trocar has traversed the abdominal wall.

Figure 5A:
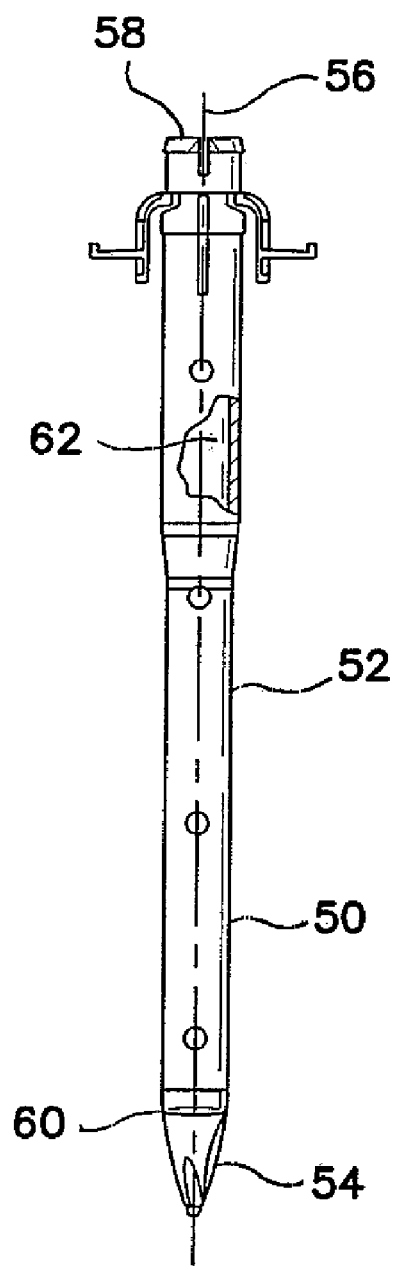
FIGS. 5A and 5B illustrate side views of an optical obturator having an integral tip and shaft.
Figure 5B:
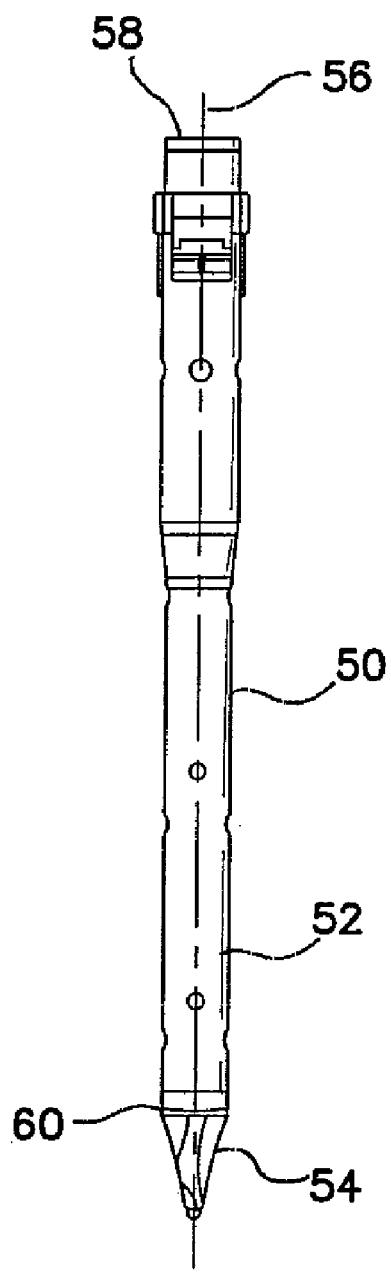
Figure 6:
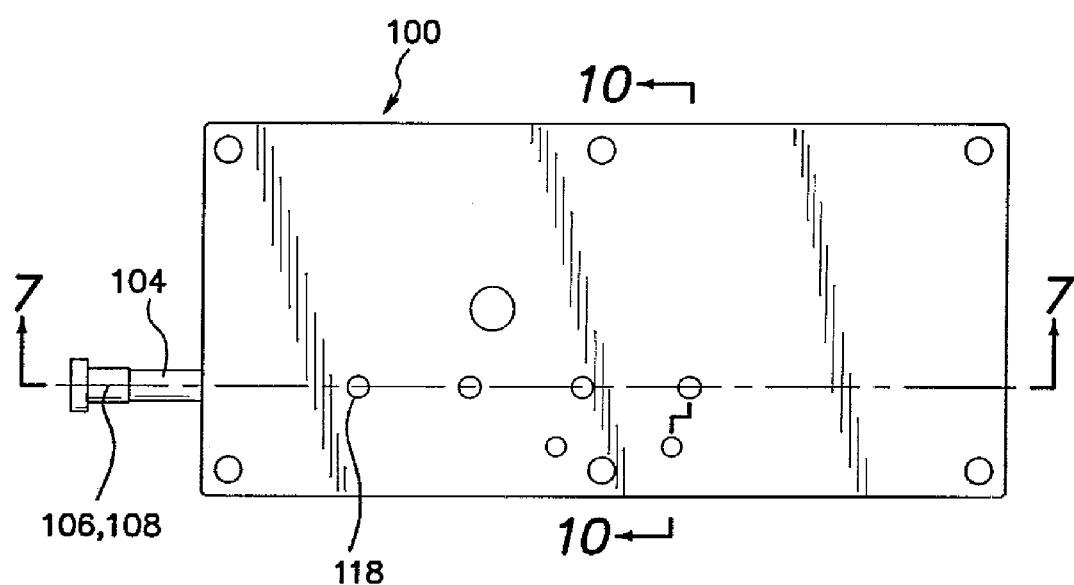
FIG. 6 is a plan view of an injection mold with a core pin that is inserted into the mold.

Referring to FIGS. 5A and 5B, the present invention includes a method for producing a single-piece, thin-walled optical obturator 50 including a thin-walled shaft portion 52 and an integral tip portion 54. The thin-walled shaft portion and the tip portion are injection molded in a single piece, thereby producing an optical obturator having an integral tip and shaft. The shaft extends along an axis 56 between a proximal end 58 and a distal end 60 with a lumen 62 extending between the proximal end and the distal end of the shaft. The lumen of the shaft is sized and configured to receive an optical instrument, such as a laparoscope (see item 26 in FIG. 3), having a distal end 64 (See FIG. 3) to receive an image of body tissue. The single-piece, thin-walled optical obturator configuration permits the lumen of the obturator shaft to remain substantially the same as the lumen on prior art single-piece obturators while reducing the outside dimensions of the shaft. Having smaller outside dimensions for the shaft serves to reduce the level of trauma to a patient during a surgical procedure. Additionally, the use of the thin-wall optical obturator permits the use of a standard size cannula in a trocar assembly.

One example of a standard size trocar cannula has an inside diameter of about 11.5 mm. If using a standard size trocar cannula, the optical obturator must be designed to fit within the standard cannula. One example of a standard laparoscope includes an outside diameter of about 10 mm along its length. Again, if a standard laparoscope is used, the optical obturator must be designed to accommodate the insertion of the standard laparoscope into the lumen 62 in the shaft of the optical obturator to enable the visualization of tissue fibers through the tip of the obturator. The wall thickness of an optical obturator is typically determined by the sizes of the trocar cannulas and the laparoscopes that have gained acceptance in the surgical environment.

An optical obturator that is to be inserted into a cannula having an inside diameter of about 11.5 mm has an outside diameter of about 11.4 mm while an optical obturator that is to accommodate the insertion of a laparoscope having an outside diameter of about 10.0 mm has an inside diameter of about 10.1 mm. In such an example, these diameters result in a very thin wall thickness for the optical obturator of about 0.65 mm. Other thin-wall optical obturators may include a wall thickness that is less than 1.11 mm. The length of some typical optical obturators ranges from about 205.0 mm to about 255.0 mm and, in some cases, as short as about 76 mm. Typically, it is very difficult to mold a complete part with such a thin wall over such lengths. Those skilled in the art will appreciate that some optical obturators are shorter than 205.0 mm or longer than 255.0 mm and are contemplated as within the scope of the present invention.

To enable production of a single-piece, thin-wall optical obturator via injection molding, one embodiment of the present invention includes the use of a high-flow or medium-flow material. In one embodiment, the material is a high-flow polymer, such as a high-flow polycarbonate material. In another embodiment, the high-flow material is capable of being sterilized, such as by gamma radiation, electron beam sterilization, or ethylene oxide sterilization. The polycarbonate material is substantially transparent to enable visualization of a body wall, hollow cavity, or body organ as the optical obturator is being placed into a patient.

Typical transparent polycarbonate materials are prone to yellowing or graying when subjected to gamma radiation or electron beam sterilization. To address the discoloration as a result of gamma radiation or electron beam sterilization, some plastic material manufacturers have added a compensating colorant, which is usually purple in color, to the base polycarbonate. These materials are specified as gamma radiation stable polycarbonates or electron beam sterilization stable polycarbonates. Prior to sterilization, components molded from gamma radiation stable or electron beam stable polycarbonates have a purple tint to them. As a result of gamma radiation or electron beam sterilization, the purple tint of the component is removed, leaving a clear, substantially non-tinted transparent component.

Melt flow rate, or melt mass-flow rate, of a plastic material is one indicator used to determine the capability of a material to flow during injection molding. Melt flow rate of a plastic material is related to material viscosity, which in turn is related to the molecular weight of the material. For a given class of polymer, such as polycarbonate, a high molecular weight material has a higher viscosity than a low molecular weight material. Also, a more viscous, high molecular weight polycarbonate material tends to have a lower melt flow rate verses a less viscous, lower molecular weight polycarbonate material.

Melt flow rate of a plastic material is measured by using a standard piston to extrude a plastic material heated to a set temperature through a standard sized die for 10 minutes and then measuring the mass of the extruded material. The melt flow rate is determined per the ISO 1133 standard and the units for melt flow rate are grams of material per 10 minutes. Polycarbonate materials with a melt flow rate of about 20 grams/10 minutes or greater permit complete filling of the mold cavity for injection molding of the thin-walled optical obturator. For low molecular weight specialty grades of polycarbonate materials, melt flow rates can be as high as 60 grams/10 minutes. By way of example, and not by way of limitation, one high-flow polycarbonate material that contains these properties and enables complete filling of the injection mold cavity to produce the single-piece, thin-wall optical obturator 50 is MAKROLON 2458-55117PR, with a melt flow rate of about 20 grams/10 minutes, which is available from Bayer Polymers.

The viscosity of a plastic material, such as polycarbonate, is directly related to the molecular weight of the material. For polymeric materials, molecular chain lengths can vary widely within a given material and chemical structure may also vary slightly from molecule to molecule. Therefore, weight average molecular weight, which is given in atomic mass units, or "amu," is used to describe a given polymer rather than molecular weight. Within a given family of polymers, such as polycarbonates, as the weight average molecular weight increases, the viscosity of the material also increases. As the viscosity of a material such as polycarbonate increases, its resistance to flow, and therefore its resistance to fill an injection mold cavity, also increases.

Polycarbonate materials with weight average molecular weights of about 24000 atomic mass units or less permit complete filling of the mold cavity for injection molding of the thin-walled optical obturator. By way of example, and not by way of limitation, one high-flow polycarbonate material that contains these properties and enables complete filling of the injection mold cavity to produce the single-piece, thin-wail optical obturator is MAKROLON 2458-55117PR, with a weight average molecular weight of about 24000 atomic mass units, which is available from Bayer Polymers.

Another measure of viscosity for a thermoplastic polymer material is the MOLDFLOW viscosity index. The MOLD-FLOW viscosity index was developed by the Moldflow Corporation as a means for using a single material property to compare the ability of materials within a given polymer family to fill an injection mold cavity. The MOLDFLOW viscosity index for a material is based on a material's actual viscosity model at a typical melt processing temperature and a standard shear rate of 1000 1/second. The units for MOLD-FLOW viscosity index are Pascal-seconds, the same as those used for dynamic viscosity. Within a given family of polymers, such as polycarbonates, as the MOLDFLOW viscosity index increases, the resistance of the material to flow and fill a mold cavity also increases. Polycarbonate materials with a MOLDFLOW viscosity index of about 196 Pascal-seconds or less at a temperature of about 300° C. permit complete filling of the mold cavity for injection molding of the thin-walled optical obturator. Satisfactory results may be obtained by injection molding the optical obturator at a temperature between about 282° C. and about 316° C. By way of example, and not by way of limitation, one high-flow polycarbonate material that contains these properties and enables complete filling of the injection mold cavity to produce the single-piece, thin-wall optical obturator is MAKROLON 2458-55117PR, with a MOLDFLOW viscosity index of about 196 Pascal-seconds at a temperature of about 300° C.

Referring to FIGS. 6, 7, 8 and 9, the injection mold 100 for producing the single-piece, thin-wall optical obturator 50 (FIGS. 5A and 5B) includes a mold cavity 102 and a core pin 104. The mold cavity produces the outside surface dimensions and details of the optical obturator and includes a longitudinal axis 106. The core pin also includes a longitudinal axis 108 and produces the inside surface dimensions and details for the optical obturator. The mold 100 may include at least two mold sections that define the mold cavity 102. The core pin 104 is positioned substantially in the center of the mold cavity. In one embodiment, the injection mold includes two mold halves 110, 112 that define the mold cavity with the core pin 104 being positioned in the mold cavity such that the axis 108 of the core pin 104 is substantially coaxial with the axis 106 of the mold cavity.

Molten polymer is injected through at least one gate 114, such as a valve gate or other mold gates that are well known in the art, into the mold cavity 102 and the material flows between the walls 116 of the mold cavity and the core pin 104. The mold 100 may include a hot runner system that facilitates maintaining the molten polymer at a temperature sufficient to promote high flow of the polymer into and through the mold cavity 102. In one embodiment, secondary core support pins 118 are included on each half 110, 112 of the mold cavity. The secondary core support pins may be designed to interlock with the core pin 104 to prevent the core pin from shifting during injection of the molten polymer into the mold cavity 102. In another embodiment, the secondary core support pins 118 may pilot into the core pin 104 to more positively position the core pin within the mold cavity. The secondary core support pins may have a substantially circular cross-section along their lengths. However, those skilled in the art will appreciate that other shapes for the cross-sections along the lengths of the secondary core support pins may be used and are contemplated as within the scope of the present invention. With the secondary core support pins in place, the resulting molded optical obturator 50 (FIGS. 5A and 5B) includes a series of holes spaced along the wall of the optical obturator.

In one embodiment, for an optical obturator having a length of about 205 mm, the injection mold 100 may include about eight (8) secondary core support pins 118, four (4) on each side, that are positioned substantially perpendicular to the core pin 104 and substantially perpendicular to the gates 114. For an optical obturator having a length of about 255 mm, the injection mold 100 may include about ten (10) secondary core support pins 118, five (5) on each side, that are positioned substantially perpendicular to the core pin 104 and substantially perpendicular to the gates 114. The secondary core support pins 118 may pilot into the core pin a depth of about 0.9 mm. However, those skilled in the art will appreciate that the secondary core support pins 118 may pilot into the core pin at a depth other than about 0.9 mm and be contemplated as within the scope of the present invention. Those skilled in the art will also appreciate that other fewer or more secondary core support pins may be used and that this too is contemplated as within the scope of the present invention. In another embodiment, the injection mold 100 may include one or more secondary core support pins 130 that are positioned substantially perpendicular to the core pin 104 and substantially parallel to the gates 114 on the same side of the mold as the gates 114.

Figure 7:
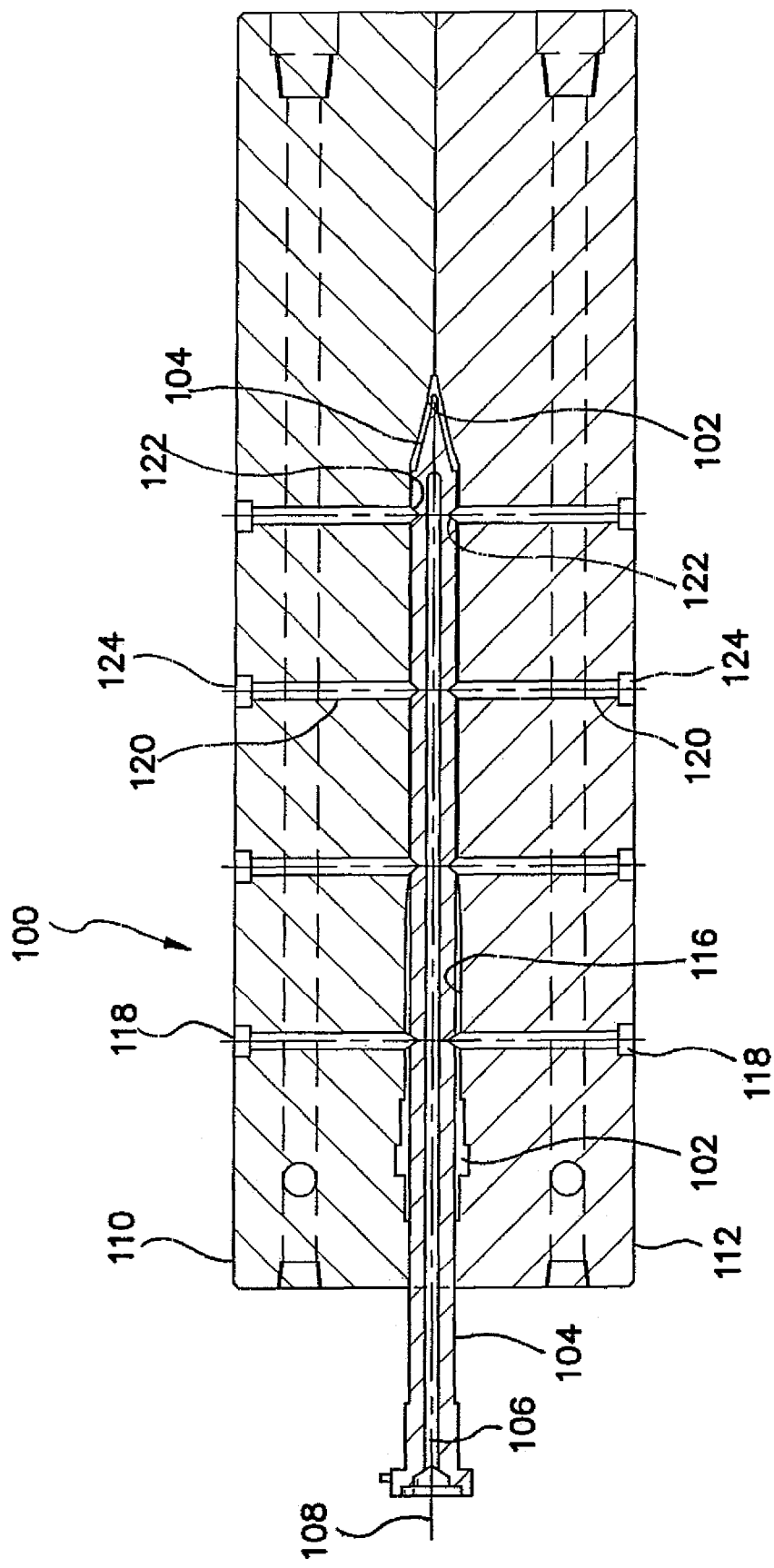
FIG. 7 is a cross-section view taken along line 7-7 of FIG. 6.
Figure 8:
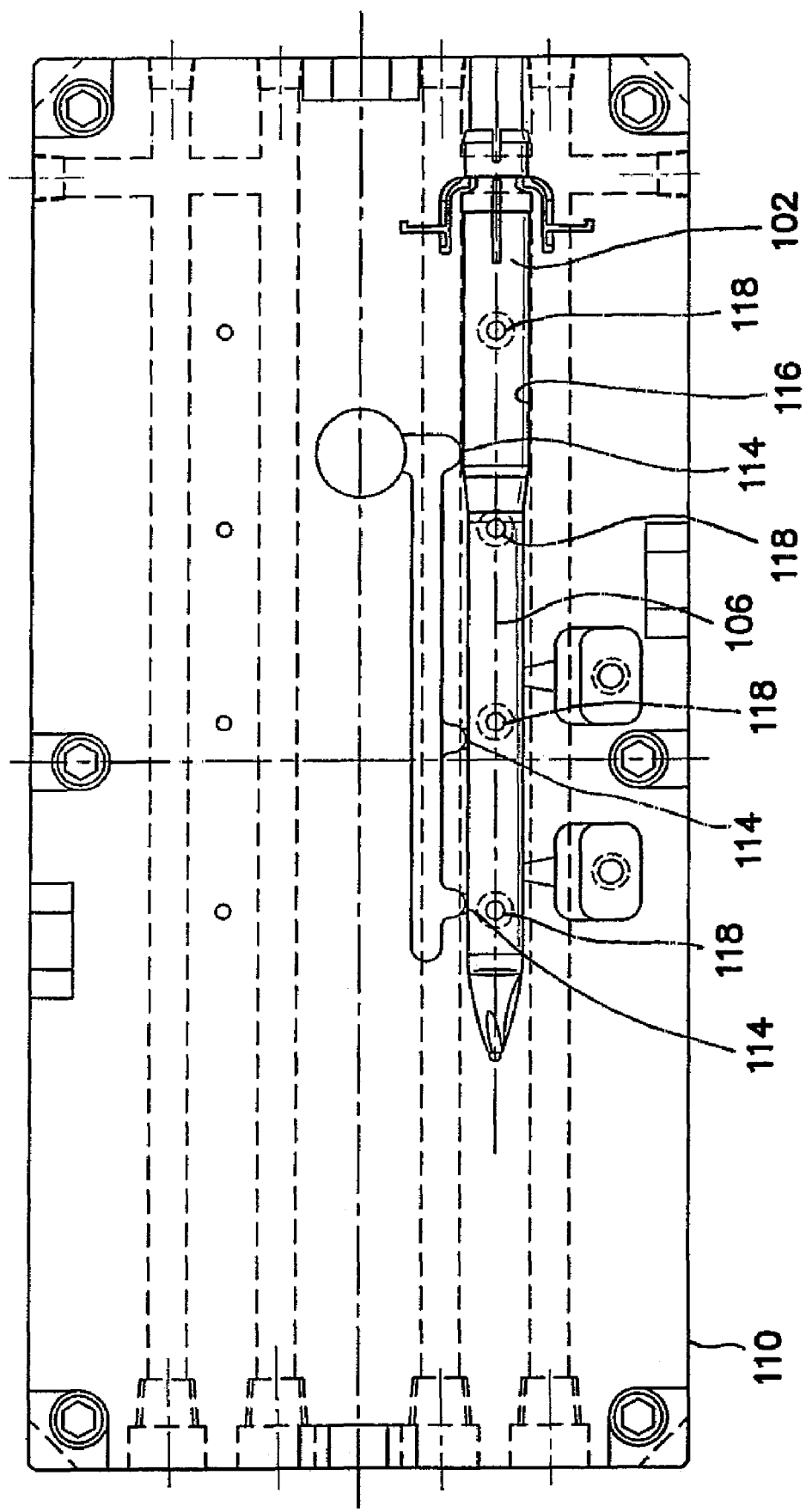
FIG. 8 is a plan view of a mold half of the injection mold of FIG. 6 depicting a mold cavity.
Figure 9:
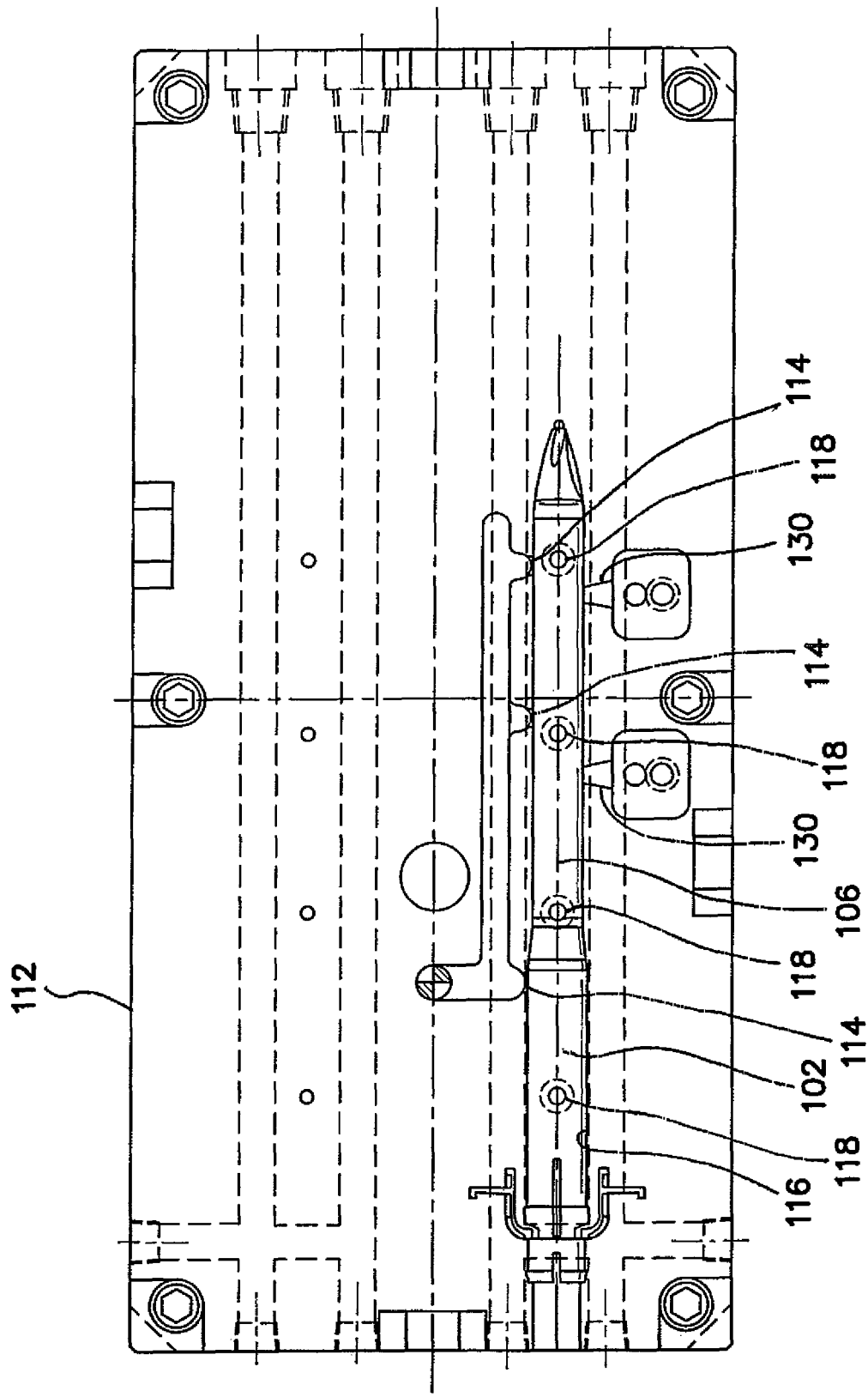
FIG. 9 is a plan view of a mold half of the injection mold of FIG. 6 depicting a mold cavity that compliments the mold cavity of the mold half of FIG. 8.

Referring to FIG. 7, in one embodiment the secondary core support pins 118 may include a screw 120 that is threaded into one of the mold halves 110, 112. An end 122 of the screw 120 that is away from the head 124 of the screw may be configured for piloting into the core pin 104. The pins 118 may be either fixed, so that they do not move in relation to the mold half in which it is installed, or adjustable to control the depth of the penetration of the pins into the core pin 104. In other embodiments, the secondary core support pins 118 may include pins that are press fitted, bonded, welded, or otherwise fixed within the mold halves 110, 112. Alternatively, the secondary core support pins 118 may be coupled to the mold halves 110, 112 by any method that is well known in the art.

Figure 10:
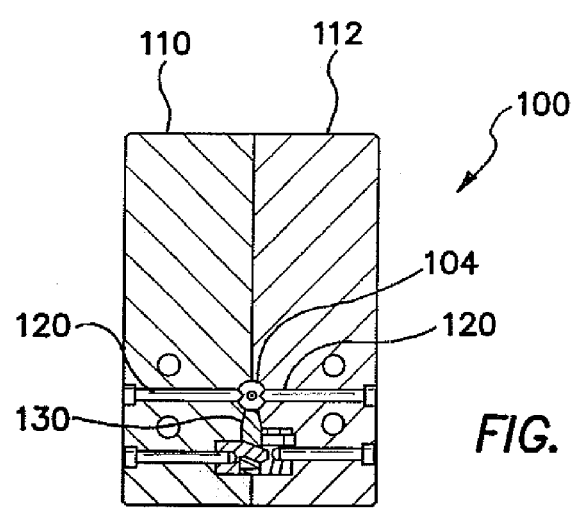
FIG. 10 is a cross-section view taken along line 10-10 of FIG. 6.

Referring to FIG. 10, the injection mold 100 may also include one or more primary core support pins 130 that are positioned substantially perpendicular to the core pin 104 and substantially parallel to the gates 114 (see FIGS. 8 and 9) on the side of the mold opposite the gates 114. Positioning primary core support pins on the side of the mold opposite the gates greatly reduces the tendency of the core pin to shift away from the gates during injection of a polymer through the gates and enables the mold cavity to completely and evenly fill resulting in a component with substantially equal wall thicknesses at any given diametral cross-section. For an optical obturator having a length of about 205 mm, the injection mold 100 may include about two (2) primary core support pins 130 positioned substantially perpendicular to the core pin 104 and substantially parallel to the gates 114 on the side of the mold opposite the gates. For an optical obturator having a length of about 255 mm, the injection mold 100 may include about three (3) primary core support pins 130 that are positioned substantially perpendicular to the core pin 104 and substantially parallel to the gates 114 on the side of the mold opposite the gates.

In one embodiment, the core pin 104 is designed such that the wall thickness at a distal tip 38 (FIG. 3) of the optical obturator is substantially equal to the wall thickness at an intermediate section 39 of the optical obturator. If the wall thickness of the distal tip of the optical obturator is substantially larger than the wall thickness of the intermediate section of the optical obturator, it may be necessary to increase the molding temperatures and pressures to completely fill the mold cavity 102, which may lead to diminished integrity of the optical integrity. Having the distal tip of the optical obturator substantially equal to the wall thickness of the intermediate section of the optical obturator allows the molding temperatures and pressures to remain lower while enabling complete filling of the mold cavity and maintains the integrity of the optical obturator.

Referring again to FIGS. 8 and 9, the injection mold 100 may include multiple gates 114, such as a valve gate or other mold gates that are well known in the art. Typical injection mold designs include a single gate orifice through which molten polymer is forced into the mold cavity. The gate serves to create shear in the molten polymer to further decrease viscosity and to aid with material flow in the mold cavity. By including multiple gates in the mold, the mold flow length increases, enabling a larger mold cavity to be completely filled more easily. In one embodiment, for an optical obturator having a length of about 205 mm, the injection mold 100 may include a series of about three (3) edge gates 114. For an optical obturator having a length of about 255 mm, the injection mold 100 may include a series of about four (4) edge gates 114. Those skilled in the art will appreciate that additional gates may be used and this is contemplated as within the scope of the present invention.

The cost to manufacture a single-piece, thin-wall optical obturator is significantly less than the cost to manufacture a prior art multiple-piece optical obturator as only one component needs to be molded and no secondary assembly operations are required for attaching the tip to the shaft. The single-piece design of the thin-wall optical obturator can be injection molded with a high-flow or medium-flow polycarbonate via a mold and an injection press in one manufacturing operation. The typical cycle time for this type of injection molding process is 15-30 seconds. By comparison, to produce a two-piece design of the prior art optical obturator, first a tip, such as a polycarbonate tip, must be injection molded and a shaft, such as a stainless steel shaft, must be fabricated. Additionally, another operation is required to bond the polycarbonate tip to the shaft. The single-piece design of the present invention includes one manufacturing operation while a two-piece design of the prior art optical obturators, as described, requires at least three manufacturing operations. Other prior art two-piece optical obturators include overmolding the tip onto the shaft, thus requiring at least two manufacturing operations.

It will be understood that many modifications can be made to the disclosed embodiments without departing from the spirit and scope of the invention. For example, various sizes of the surgical device are contemplated as well as various types of constructions and materials. It will also be apparent that many modifications can be made to the configuration of parts as well as their interaction. For these reasons, the above description should not be construed as limiting the invention, but should be interpreted as merely exemplary of the embodiments.

The invention claimed is:

1. A method for manufacturing a thin-wall, single-piece optical obturator having a wall thickness less than 1.11 mm, the obturator including an integral tip and shaft, the shaft extending along an axis between a proximal end and a distal end with a lumen therebetween, the lumen being sized and configured to receive an optical instrument having a distal end for receiving an image of body tissue, comprising:
   providing an injection mold, the injection mold including,
      a mold cavity defining an outside surface of the single-piece optical obturator,
      a core pin positioned within the mold cavity, the core pin defining an inside surface of the single-piece optical obturator, the distance between an outer surface of the core pin and the surface of the mold cavity being 1.11 mm or less,
      at least one gate extending into the mold cavity, and
      at least one core support pin for supporting the core pin within the mold cavity, the at least one core support pin being positioned between a surface of the mold cavity and a surface of the core pin and on the side substantially opposite the at least one gate; and
   injecting a transparent, molten polymeric material having high flow properties into the injection mold such that the polymeric material flows between the surface of the mold cavity and the core pin.

2. The method of claim 1, further comprising sterilizing the optical obturator.

3. The method of claim 2, wherein the sterilizing step includes sterilizing with one of gamma radiation, electron beam sterilization and ethylene oxide sterilization.

4. The method of claim 1, wherein the injecting step includes injecting a high-flow polycarbonate material.

5. The method of claim 4, wherein the injecting step includes injecting a high-flow polycarbonate material that is capable of being sterilized by one of gamma radiation and electron beam sterilization.

6. The method of claim 5, wherein the injecting step includes injecting a high-flow polycarbonate material having a compensating colorant.

7. The method of claim 4, wherein the injecting step includes injecting a high-flow polycarbonate material that is capable of being sterilized by ethylene oxide sterilization.

8. The method of claim 4, wherein the injecting step includes injecting a high-flow polycarbonate material having a melt flow rate of about 20 grams/10 minutes or greater.

9. The method of claim 8, wherein the injecting step includes injecting a high-flow polycarbonate material having a melt flow rate between 20 grams/10 minutes and 60 grams/10 minutes.

10. The method of claim 4, wherein the injecting step includes injecting a high-flow polycarbonate material having a weight average molecular weight of about 24000 atomic mass units or lower.

11. The method of claim 4, wherein the injecting step includes injecting a high-flow polycarbonate material having a MOLDFLOW viscosity index of about 196 Pascal-seconds or less at a temperature of about 300° C.

12. The method of claim 11, wherein the injecting step includes injecting a high-flow polycarbonate material having a MOLDFLOW viscosity index of about 196 Pascal-seconds or less at a temperature between 282° C. and 316° C.

13. The method of claim 1, wherein the providing step includes providing an injection mold having at least two mold sections defining the mold cavity and the core pin being positioned substantially in the center of the mold cavity.

14. The method of claim 1, wherein the providing step includes providing an injection mold having two mold halves.

15. The method of claim 14, wherein the providing step includes providing an injection mold having two mold halves defining the mold cavity and the core pin being positioned in the mold cavity such that an axis of the core pin is positioned substantially coaxially with an axis of the mold cavity.

16. The method of claim 14, wherein the providing step includes providing an injection mold having two mold halves and a plurality of secondary core support pins included on each half of the mold cavity and distributed along the length of the mold cavity.

17. The method of claim 16, wherein the providing step includes providing an injection mold having secondary core support pins that interlock with the core pin.

18. The method of claim 16, wherein the providing step includes providing an injection mold having secondary core support pins that are adapted to pilot into the core pin.

19. The method of claim 18, wherein the providing step includes providing an injection mold having secondary core support pins that are adapted to pilot into the core pin to a depth of about 0.9 mm.

20. The method of claim 16, wherein the providing step includes providing an injection mold having longitudinal secondary core support pins that have a substantially circular cross-section along their lengths.

21. The method of claim 16, wherein the providing step includes providing an injection mold having four secondary core support pins on each mold half, the secondary core support pins being positioned substantially perpendicular to the core pin and substantially perpendicular to the at least one gate.

22. The method of claim 16, wherein the providing step includes providing an injection mold having five secondary core support pins on each mold half, the secondary core support pins being positioned substantially perpendicular to the core pin and substantially perpendicular to the at least one gate.

23. The method of claim 16, wherein the providing step includes providing an injection mold having secondary core support pins in the form of screws.

24. The method of claim 23, wherein the providing step includes providing an injection mold having the ends of the screws that are opposite the heads of the screws configured for piloting into the core pin.

25. The method of claim 16, wherein the providing step includes providing an injection mold having the secondary core support pins fixedly coupled to the mold halves.

26. The method of claim 16, wherein the providing step includes providing an injection mold having the secondary core support pins adjustably coupled to the mold halves.

27. The method of claim 16, wherein the providing step includes providing an injection mold having secondary core support pins positioned substantially perpendicular to the core pin and substantially parallel to the at least one gate on the same side of the mold as the at least one gate.

28. The method of claim 1, the providing step including providing an injection mold wherein the at least one core support pin includes at least one primary core support pin that is positioned substantially perpendicular to the core pin and substantially parallel to the at least one gate on the side of the mold opposite the at least one gate.

29. The method of claim 28, wherein the providing step includes the at least one primary core support pin including two primary core support pins distributed along the length of the mold cavity.

30. The method of claim 28, wherein the providing step includes the at least one primary core support pin including three primary core support pins distributed along the length of the mold cavity.

31. The method of claim 1, wherein the providing step includes providing an injection mold having a plurality of gates distributed along the length of the mold cavity.

32. The method of claim 31, wherein the providing step includes providing an injection mold having a series of three gates.

33. The method of claim 31, wherein the providing step includes providing an injection mold having a series of four gates.

34. A method for manufacturing a thin-wall, single-piece optical obturator having a wall thickness less than 1.11 mm, the obturator including an integral tip and shaft, the shaft extending along an axis between a proximal end and a distal end with a lumen therebetween, the lumen being sized and configured to receive an optical instrument having a distal end for receiving an image of body tissue, comprising:

providing an injection mold, the injection mold including,
two mold halves,
a mold cavity having a longitudinal axis, the mold cavity defining an outside surface of the single-piece optical obturator, the mold cavity being defined by the two mold halves,
a core pin having a longitudinal axis, the core pin defining an inside surface of the single-piece optical obturator, the core pin being positioned in the mold cavity such that the longitudinal axis of the core pin is positioned substantially coaxial with the longitudinal axis of the mold cavity, the distance between an outer surface of the core pin and the surface of the mold cavity being 1.11 mm or less,
a plurality of gates extending into the mold cavity, the gates being distributed along the length of the mold cavity,
at least one primary core support pin for supporting the core pin within the mold cavity between a surface of the mold cavity and a surface of the core pin, the at least one primary core support pin being positioned substantially perpendicular to the core pin and substantially parallel to the at least one gate on the side of the mold opposite the at least one gate, and a plurality of secondary core support pins included in each half of the mold cavity, the secondary core support pins supporting the core pin within the mold cavity between a surface of the mold cavity and a surface of the core pin, the secondary core support pins being distributed along the length of the mold cavity, each of the plurality of secondary core support pins being positioned substantially perpendicular to the core pin and substantially perpendicular to the at least one gate; and injecting a transparent, molten polycarbonate material having high flow properties into the injection mold such that the polycarbonate material flows between the surface of the mold cavity and the core pin.

35. The method of claim 34, wherein the injecting step includes injecting a material having a melt flow rate of about 20 grams/10 minutes or greater.

36. The method of claim 35, wherein the injecting step includes injecting a material having a melt flow rate between 20 grams/10 minutes and 60 grams/10 minutes.

37. The method of claim 34, wherein the injecting step includes injecting a material having a weight average molecular weight of about 24000 atomic mass units or lower.

38. The method of claim 34, wherein the injecting step includes injecting a material having a MOLDFLOW viscosity index of about 196 Pascal-seconds or less at a temperature of about 300° C.

39. The method of claim 38, wherein the injecting step includes injecting a material having a MOLDFLOW viscosity index of about 196 Pascal-seconds or less at a temperature between 282° C. and 316° C.

40. The method of claim 34, wherein the providing step includes providing an injection mold having secondary core support pins that interlock with the core pin.

41. The method of claim 34, wherein the providing step includes providing an injection mold having secondary core support pins that are adapted to pilot into the core pin.

42. The method of claim 41, wherein the providing step includes providing an injection mold having secondary core support pins that are adapted to pilot into the core pin to a depth of about 0.9 mm.

43. The method of claim 34, wherein the providing step includes providing an injection mold having secondary core support pins that have a substantially circular cross-section along their lengths.

44. The method of claim 34, wherein the providing step includes providing an injection mold having four secondary core support pins on each mold half.

45. The method of claim 34, wherein the providing step includes providing an injection mold having five secondary core support pins on each mold half.

46. The method of claim 34, wherein the providing step includes providing an injection mold having secondary core support pins in the form of screws.

47. The method of claim 46, wherein the providing step includes providing an injection mold having the ends of the screws that are opposite the heads of the screws configured for piloting into the core pin.

48. The method of claim 34, wherein the providing step includes providing an injection mold having the secondary core support pins fixedly coupled to the mold halves.

49. The method of claim 34, wherein the providing step includes providing an injection mold having the secondary core support pins adjustably coupled to the mold halves.

50. The method of claim 34, wherein the providing step includes the at least one primary core support pin including two primary core support pins distributed along the length of the mold cavity.

51. The method of claim 34, wherein the providing step includes the at least one primary core support pin including three primary core support pins distributed along the length of the mold cavity.

52. The method of claim 34, wherein the providing step includes providing an injection mold having a series of three gates distributed along the length of the mold cavity.

53. The method of claim 34, wherein the providing step includes providing an injection mold having a series of four gates distributed along the length of the mold cavity.

54. A method for manufacturing a thin-wall, single-piece optical obturator having a wall thickness less than 1.11 mm, the obturator including an integral tip and shaft, the shaft extending along an axis between a proximal end and a distal end with a lumen therebetween, the lumen being sized and configured to receive an optical instrument having a distal end for receiving an image of body tissue, comprising:

providing an injection mold, the injection mold including,
a mold cavity defining an outside surface of the single-piece optical obturator,
a core pin positioned within the mold cavity, the core pin defining an inside surface of the single-piece optical obturator, the distance between an outer surface of the core pin and the surface of the mold cavity being 1.11 mm or less, and
at least one core support pin for supporting the core pin within the mold cavity, the at least one core support pin being positioned between a surface of the mold cavity and a surface of the core pin; and injecting a transparent, molten polymeric material having high flow properties into the injection mold such that the polymeric material flows between the surface of the mold cavity and the core pin.

55. A method for manufacturing a thin-wall, single-piece optical obturator having a wall thickness less than 1.11 mm, the obturator including an integral tip and shaft, the shaft extending along an axis between a proximal end and a distal end with a lumen therebetween, the lumen being sized and configured to receive an optical instrument having a distal end for receiving an image of body tissue, comprising:

providing an injection mold, the injection mold including,
a mold cavity defining an outside surface of the single-piece optical obturator,
a core pin positioned within the mold cavity, the core pin defining an inside surface of the single-piece optical obturator, the distance between an outer surface of the core pin and the surface of the mold cavity being 1.11 mm or less,
at least one gate extending into the mold cavity, and
at least one core support pin for supporting the core pin within the mold cavity, the at least one core support pin being positioned between a surface of the mold cavity and a surface of the core pin and on the side substantially opposite the at least one gate; and injecting a transparent, molten polymeric material into the injection mold such that the polymeric material flows between the surface of the mold cavity and the core pin.

* * * * *